(12) United States Patent  
Mantese et al.

(10) Patent No.: US 9,585,808 B2  
(45) Date of Patent: Mar. 7, 2017

(54) IMPLANTABLE DEVICE FOR PULSATILE COMPRESSION

(71) Applicants: Lucymarie Mantese, Redwood City, CA (US); Vito A. Mantese, Columbia, IL (US); Annamarie Mantese, Redwood City, CA (US)

(72) Inventors: Lucymarie Mantese, Redwood City, CA (US); Vito A. Mantese, Columbia, IL (US); Annamarie Mantese, Redwood City, CA (US)

(*) Notice: Subject to any disclaimer, the term of this patent is extended or adjusted under 35 U.S.C. 154(b) by 929 days.

(21) Appl. No.: 13/889,450

(22) Filed: May 8, 2013

(65) Prior Publication Data

US 2014/0336551 A1 Nov. 13, 2014

(51) Int. Cl.
- *A61H 9/00* (2006.01)
- *A61B 17/12* (2006.01)
- *A61B 17/122* (2006.01)
- *A61B 17/135* (2006.01)

(52) U.S. Cl.
CPC ......... *A61H 9/0007* (2013.01); *A61B 17/122* (2013.01); *A61B 17/12009* (2013.01); *A61B 17/135* (2013.01); *A61H 9/00* (2013.01); *A61H 9/005* (2013.01); *A61H 9/0078* (2013.01); *A61H 2201/0103* (2013.01); *A61H 2201/5058* (2013.01); *A61H 2201/5084* (2013.01); *A61H 2201/5097* (2013.01)

(58) Field of Classification Search
CPC ........ A61H 9/00; A61H 9/0007; A61H 9/005; A61H 9/0071; A61H 9/0078; A61H 9/0085; A61H 9/0092; A61H 2201/0103; A61H 2201/1409; A61H 2201/5056; A61H 2201/5097; A61H 2201/5084; A61H 2201/5058; A61M 25/1018; A61M 25/10

USPC ......... 604/96.01, 97.01, 98.01, 99.01–99.03; 606/194

See application file for complete search history.

(56) References Cited

U.S. PATENT DOCUMENTS 3,863,622 A * 2/1975 Buuck ..................... A61F 2/004  
                                                                               128/DIG. 25  
4,871,351 A * 10/1989 Feingold ............ A61B 5/14532  
                                                                               128/DIG. 12

(Continued)

Primary Examiner — Justine Yu  
Assistant Examiner — Tu Vo  
(74) Attorney, Agent, or Firm — Kenneth Kohn (57) ABSTRACT

A method of treating venous insufficiency and lymphedema in an individual by placing pulsatile, localized pressure or compression on deep veins and subcutaneous tissue by inflating and deflating volume-changing members implanted within the individual. A method of potentiating venous circulation, by placing pulsatile, localized pressure that compresses the deep veins by expanding and contracting volume-changing members located between the fascia and muscular compartment, such that the increase in volume from the volume-changing members is transferred to deep veins, and augmenting the effects of muscle contractions around the deep veins and improving blood circulation. A method of potentiating lymphatic circulation. A method of potentiating venous and lymphatic circulation. A pulsatile pressure implant including at least one volume-changing member in electronic connection with an electronic-controlled microprocessor.

23 Claims, 5 Drawing Sheets

(56) References Cited

U.S. PATENT DOCUMENTS

| | | | | |
|---|---|---|---|---|
| 4,958,630 | A * | 9/1990 | Rosenbluth | A61B 17/12 600/40 |
| 5,695,468 | A * | 12/1997 | Lafontaine | A61M 25/1018 604/96.01 |
| 5,885,244 | A * | 3/1999 | Leone | A61M 25/1018 604/131 |
| 6,551,280 | B1 * | 4/2003 | Knighton | A61B 17/12118 601/152 |
| 8,567,407 | B1 * | 10/2013 | Kimani Mwangi | A61F 5/56 128/848 |
| 2005/0131385 | A1 * | 6/2005 | Bolling | A61M 25/003 604/509 |
| 2005/0187500 | A1 * | 8/2005 | Perry | A61H 9/0078 601/152 |
| 2006/0178604 | A1 * | 8/2006 | Alderman | A61H 9/0078 601/149 |
| 2007/0179421 | A1 * | 8/2007 | Farrow | A61H 9/005 602/75 |
| 2008/0021266 | A1 * | 1/2008 | Laham | A61F 2/2481 600/37 |
| 2008/0071135 | A1 * | 3/2008 | Shaknovich | A61B 5/042 600/17 |
| 2008/0275295 | A1 * | 11/2008 | Gertner | A61B 17/00234 600/37 |
| 2010/0331816 | A1 * | 12/2010 | Dadino | A61K 31/337 604/509 |
| 2011/0196271 | A1 * | 8/2011 | Forsell | A61F 2/26 601/46 |
| 2012/0053514 | A1 * | 3/2012 | Robinson | A61M 5/14276 604/65 |
| 2012/0065561 | A1 * | 3/2012 | Ballas | A61H 9/0021 601/152 |
| 2012/0078145 | A1 * | 3/2012 | Malhi | A61H 9/0092 601/149 |
| 2012/0078146 | A1 * | 3/2012 | Deshpande | A61H 9/0078 601/151 |
| 2012/0220905 | A1 * | 8/2012 | Avni | A61M 16/0006 601/2 |
| 2013/0035655 | A1 * | 2/2013 | Nakamura | A61F 13/36 604/360 |
| 2014/0094726 | A1 * | 4/2014 | Malhi | A61H 9/00 601/152 |

* cited by examiner

IMPLANTABLE DEVICE FOR PULSATILE COMPRESSION

BACKGROUND OF THE INVENTION

1. Technical Field

The present invention relates to devices for the treatment of venous insufficiency and lymphedema.

2. Background Art

A healthy vein contains valves that open and close to assist the return of blood to the heart. Venous insufficiency refers to damaged or diseased valves that can result in a backward flow of blood, a condition known as venous reflux. This reflux causes blood to pool, often in the lower legs, and can lead to symptoms of pain and swelling. Chronic venous insufficiency (CVI) is a long-term, persistent state of venous reflux and associated symptoms. Advanced stages can lead to inflammation, deep vein thrombosis (DVTs, known as blood clots), ulcers and limb amputation. These symptoms can be unbearable and affect daily activities. Varicose veins are often a precursor or symptom of CVI. Valves become damaged or diseased for many reasons, including obesity, heredity, prolonged standing and inactivity. There are currently an estimated 24 million people in the United States with varicose veins. An estimated 6 million individuals in the United States have severe symptoms of CVI ranging from skin changes to ulcerations. Annual treatment costs of venous ulcers in the United States are estimated to be $3 billion with a loss of 2 million work days as a result.

Lymphedema is a condition where swelling occurs due to an accumulation of lymphatic fluid often in the legs and arms that is unable to drain back into the blood circulation because of a compromised lymphatic system. As the lymph fluid pools a high concentration of bacteria may form and the swollen area becomes more susceptible to infection. Patients with lymphedema experience pain and are at risk of severe infection. Similar to venous insufficiency, lymphedema occurs for a variety of reasons including, obesity, heredity, and inactivity. Lymphedema is also known to occur after certain cancer surgeries, such as breast cancer, where the lymph nodes are disrupted due to radiation treatments. It is estimated that 3 to 5 million people in the United States experience lymphedema.

Even with the high incidence of venous insufficiency and lymphedema, the existing treatment options available are ineffective and outdated, especially given the technological advances in electronics and hardware within the last decade. In addition, chronic conditions of these disease states mean that the patient will need life-long therapies to treat the symptoms. Existing treatments to reduce the swelling associated with venous insufficiency and lymphedema are often difficult to apply, uncomfortable, and/or render the user immobile. The result is that the user often abandons treatment and the swelling persists. Existing treatments include, but are not limited to, elastic compression stockings, inelastic compression bandages, and external compression pumps. Elastic compression stockings have the complication in that they are very difficult for the user to pull them over the swollen area. The stocking is such a tight fit to begin with that the user struggles to pre-compress the swollen area so that it can slide into the stocking. Further, in hot environments, the stockings are insufferable. Often the patients are non-compliant with elastic compression stocking treatments. Inelastic compression bandages are wraps that are similar to wearing a cast and are normally applied by a certified technician. The user must go to a particular venue or clinic where the wraps are applied. The user's mobility is limited by the wraps and they are unable to bathe the wrapped area during treatment. Often the skin becomes rough, eczema forms and the area becomes odorous. The treatment is approximately a 2-week cycle that includes removing and rewrapping the swollen area. External compression pumps require a cumbersome pumping unit and a power outlet to inflate a sleeve or boot that is placed over the swollen area. The treatments can be done at home; however, an approximate treatment regiment requires one-hour sessions 5 days a week for 35 sessions. These units require that the user be immobile during the treatment period.

U.S. Patent Application Publication No. 2008/0071135 to Shaknovich discloses a treatment strategy for treatment of elevated pressure in a body conduit, such as a pulmonary vein, with a prosthetic partitioning device that permits coaxial attachment to the body conduit, e.g. the pulmonary vein, as well as delivery systems, and strategies for use thereof. A control device configured to transmit signals to the prosthetic device to effectuate the repetitive transition between a first, less restricted flow configuration and a second, restricted flow configuration is described. A sensor device can be provided for monitoring physiological parameters of the patient, and can provide signals to the control device for effectuating the transition between the first and second configuration. The prosthetic partitioning device can include one or more inflatable members (shown at 20 in the figures in the '135 application) that are supplied with gas or fluid by an implantable pump via a supply line (shown at 26 in the '135 application). A control device (shown at 14 in the '135 application) controls the configuration of the prosthetic partitioning device between less and more restriction of flow.

U.S. Patent Application Publication No. 2009/0248142 to Perkins, et al. discloses methods and systems for improving the competency of a venous valve wherein one or more compressor(s) (e.g., space occupying material(s) or implantable device(s)) is/are delivered to one or more location(s) adjacent to a venous valve to compress the venous valve in a manner that causes one or both leaflets of the valve to move toward the other, thereby improving closure or coaptation of the valve leaflets. The compressor(s) can be delivered by an open surgical approach, by a direct percutaneous approach or by a transluminal catheter-based approach. The compressor can be an implantable, inflatable member filled with solid, liquid, gaseous, or gelatinous material. The device is inserted in a contracted state and once in place is activated to be in an expanded state. However, once expanded, the compressor does not again retract, and there is no control to manipulate the configuration of the compressor.

It is important to note that the prior art prosthetic devices are required to be attached directly to the veins necessitating major invasive surgery in order for the devices to be implanted. For example, the motivation of the '135 application to Shaknovich is for the prosthetic to be clamped to the pulmonary vein. There remains a need for a prosthetic device that does not require direct access to the veins in order to generate therapeutic compression and that is a minimally invasive surgical procedure. There remains a need for a treatment of venous insufficiency and lymphedema that is easy to use, easier to implant, and effective that overcomes the deficiencies of the prior art.

SUMMARY OF THE INVENTION

The present invention provides for a method of treating venous insufficiency and lymphedema in an individual, by placing pulsatile, localized pressure that compresses the deep veins and subcutaneous tissue by expanding and contracting volume-changing members implanted within the individual.

The present invention provides for a method of potentiating venous circulation, by placing pulsatile, localized pressure that compresses the deep veins by expanding and contracting volume-changing members located between the fascia and muscular compartment, such that the increase in volume from the volume-changing members is transferred to deep veins, and augmenting the effects of muscle contractions around the deep veins and improving blood circulation.

The present invention provides for a method of potentiating lymphatic circulation, by placing pulsatile, localized pressure that compresses the subcutaneous tissue by expanding and contracting volume-changing members positioned between the fascia and subcutaneous tissue, such that the increase in volume from the volume-changing members is transferred to the subcutaneous tissue, optionally using a lightweight non-stretchable, non-compressive outer garment to contain the pressure from the increase in volume from the volume-changing members to the subcutaneous tissue, and supplementing muscle contractions and improving lymphatic flow.

The present invention further provides for a method of potentiating venous and lymphatic circulation, by placing pulsatile, localized pressure that compresses the deep veins and subcutaneous tissue by creating an incision in the fascia and expanding and contracting volume-changing members located between the fascia and muscular compartment, such that the increase in volume from the volume-changing members is transferred to deep veins and subcutaneous tissue, optionally using a lightweight non-stretchable, non-compressive outer garment to contain the pressure from the increase in volume from the volume-changing members to the deep veins and subcutaneous tissue, and augmenting the effects of muscle contractions around the deep veins and improving blood circulation and lymphatic flow.

The present invention also provides for a pulsatile pressure implant including at least one expandable mechanism for placing pulsatile, localized pressure on deep veins and subcutaneous tissue in electronic connection with microprocessor-controlled electronics.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

The present invention provides for a pulsatile pressure implant, shown generally at 10 in the FIGURES. The pulsatile pressure implant 10 includes at least one volume-changing member 12 in electronic connection with microprocessor-controlled electronics 14 and in fluid or gaseous connection with a pump 16 through tubing 18. The pulsatile pressure implant 10 is generally used to treat venous insufficiency and lymphedema by placing pulsatile, localized pressure (i.e. compression) within an extremity to compensate for faulty venous valves and a compromised lymphatic system.

Figure 8:
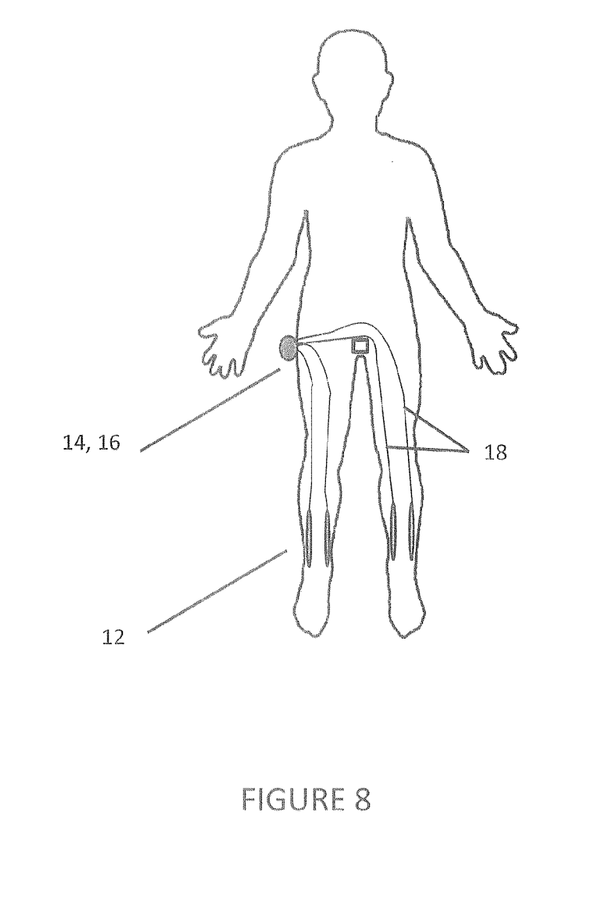
FIG. 8 is an illustration of the pulsatile pressure implant with the pump and electronics worn externally.
Figure 9:
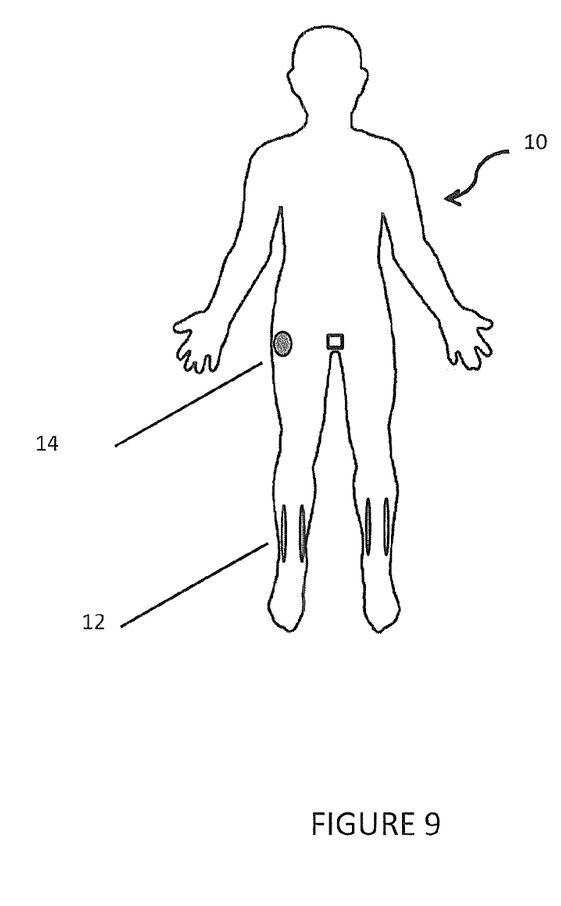
FIG. 9 is an illustration of the pulsatile pressure implant with the electronics communicating wirelessly to smart material of the volume-changing members.

The volume-changing members 12 are preferably in the form of inflatable balloons, as shown in FIGS. 1-8. However, any other suitable volume-changing member 12 that has the ability to expand and contract can be used, such as an inflatable or volume-changing member controlled by springs, magnets, temperature, or electronics. The volume-changing members 12 can be made of a biocompatible material that is able to change volume (such as by inflation or deflation). For example, the volume-changing members 12 can be made of plastic, silicone, elastomers, or any other suitable material. The volume-changing members 12 can also be made of a volume-changing material, as shown in FIG. 9. Volume-changing materials referred to herein are known in the trade as "smart materials" that are designed to characteristically change in response to external stimuli such as temperature, pH, magnetic fields, or voltage. Examples of such smart materials include, but are not limited to, piezoelectrics, shape memory alloys and shape-memory polymers. Therefore, a pulsatile compression can be generated by, for example, modulating the temperature, pH, magnetic field, or voltage. The volume-changing materials can be activated wirelessly or through implanted wires with the electronics 14. The tubing 18 is optional with the volume-changing materials depending on how they are activated. Preferably, the volume-changing members 12 are 8 mm diameter by 80 mm in length; but other sizes can be used to suit the individual's anatomy.

Preferably, two volume-changing members 12 are used in the present invention; however a single volume-changing member 12 or multiple volume-changing members 12 can also be used. The volume-changing members 12 are implanted in each extremity (legs, arms) as needed by the individual. The volume-changing members 12 can be implanted in a single leg, both legs, a single arm, both arms, or combinations of the above according to the needs of the individual. Placement of the volume-changing members 12 is further described below.

The volume-changing members 12 can include a large fill port 22 in order to minimize the inflation/deflation pressure.

A pressure relief can be used to prevent over-inflation of the extremity by the volume-changing members.

The volume-changing members 12 can include radiopaque markers to assist in placement within the anatomy and post-procedural diagnostics.

The volume-changing members can be inserted into the extremity using a delivery system similar, although not limited to, those used for percutaneous introduction of pacemaker leads or catheters.

The volume-changing members 12 can be drug-coated in order to treat areas of contact. The drug coating can include anti-pain agents or anti-inflammation agents. The anti-inflammatory or anti-pain agent can be non-steroidal anti-inflammatory drugs (NSAIDS) such as, but not limited to, acetaminophen, salicylates (aspirin, diflunisal, salsalate), acetic acid derivatives (indomethacin, ketorolac, sulindac etodolac, diclofenac, nabumetone), propionic acid derivatives (ibuprofen, naproxen, flurbiprofen, ketoprofen, oxaprozin, fenoprofen, loxoprofen), fenamic acid derivatives (meclofenamic acid, mefenamic acid, flufenamic acid, tolfenamic acid), oxicam (enolic acid) derivatives (piroxicam, meloxicam, tenoxicam, droxicam, lornoxicam, isoxicam), arylalkanoic acid derivatives (tolmetin); or selective COX-2 inhibitors (celecoxib, rofecoxib, valdecoxib, parecoxib, lumiracoxib, etoricoxib, firocoxib). The anti-inflammatory or anti-pain agent can also be steroids such as, but not limited to, corticosteroids (hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, dexamethasone, fluocortolone, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, or fluprednidene acetate). The anti-inflammatory or anti-pain agent can further be immune selective anti-inflammatory derivatives (ImSAIDs) such as, but not limited to, submandibular gland peptide T (SGp-T) and derivatives phenylalanine-glutamine-glycine (FEG) and its D-isomeric form (feG).

The volume-changing members 12 can also or alternatively be coated with a hydrophilic material in order to promote fluid uptake, especially when the pump 16 is used with a hydrophilic strip as described below.

The volume-changing members 12 can be single chambered or multi-chambered. A single or multi-chambered, volume-charging member 12 can provide pulsatile pressure. A multi-chambered volume-changing member 12 is useful in order to achieve a gradient pressure (also described below). The multi-chambered volume-changing member 12 can be segmented with varying diameters of inflation, providing segmented pressure. The individual chambers may be sequentially inflated to produce a "milking" effect on the blood and lymphatic fluid.

The microprocessor-controlled electronics 14 contain any necessary programs and algorithms for operating the pulsatile pressure implant 10, as well as necessary parameters for operation, such as pressure amplitude and frequency. Preferably, the microprocessor-controlled electronics 14 and the pump 16 are implanted remote from the volume-changing members 12, such as in the upper thigh (as in FIG. 2). However, implantation can occur at any suitable location. The microprocessor-controlled electronics 14 can also be external to the body as shown in FIG. 8, but still electronically connected to the volume-changing members 12 within the body. The microprocessor-controlled electronics 14 further include a battery and power load (not shown). The power load allows the batteries to be recharged wirelessly and externally. Furthermore, the microprocessor-controlled electronics 14 can be controlled wirelessly and remotely (as shown in FIG. 9). This allows the prescribing physician during an office visit to change the compression levels as symptoms change with treatment. For example, as swelling decreases the pressure amplitude and frequency can be adjusted by modifying the feedback values for the amplitude and frequency of inflation of the volume-changing members 12.

Figure 2:
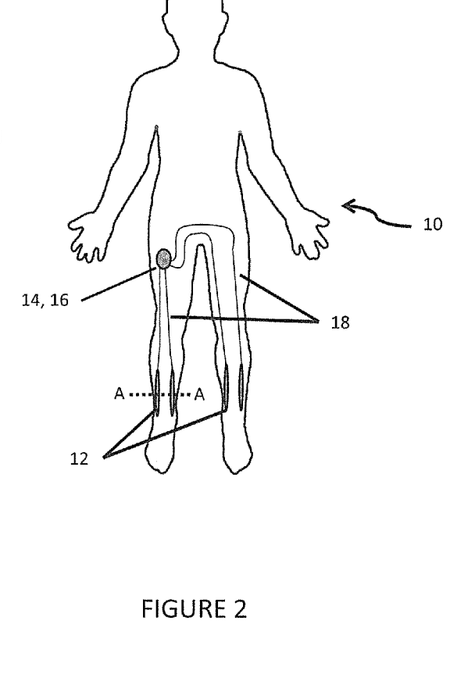
FIG. 2 is an illustration of the pulsatile pressure implant as applied to the lower extremity of an individual to target compression to the deep veins for symptoms related to venous insufficiency.
Figure 4:
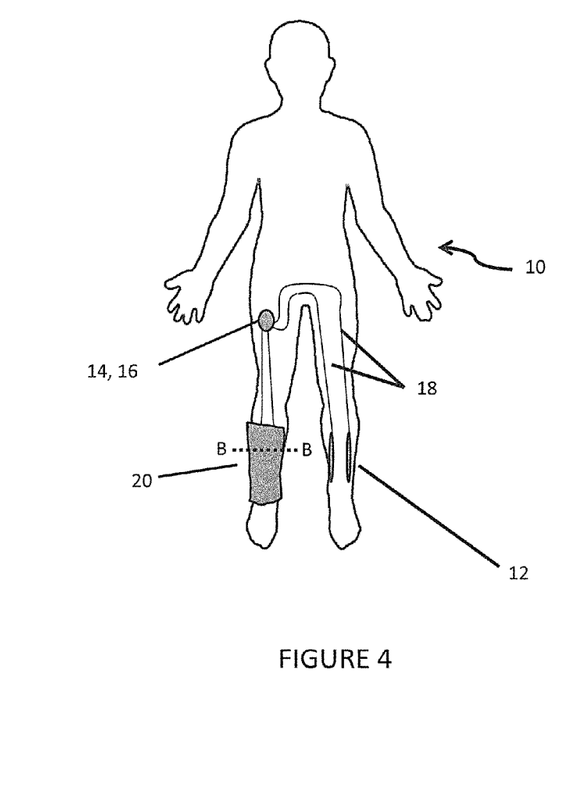
FIG. 4 is an illustration of the pulsatile pressure implant as applied to the lower extremity of an individual to target compression to the subcutaneous tissue for symptoms related to lymphedema.
Figure 5:
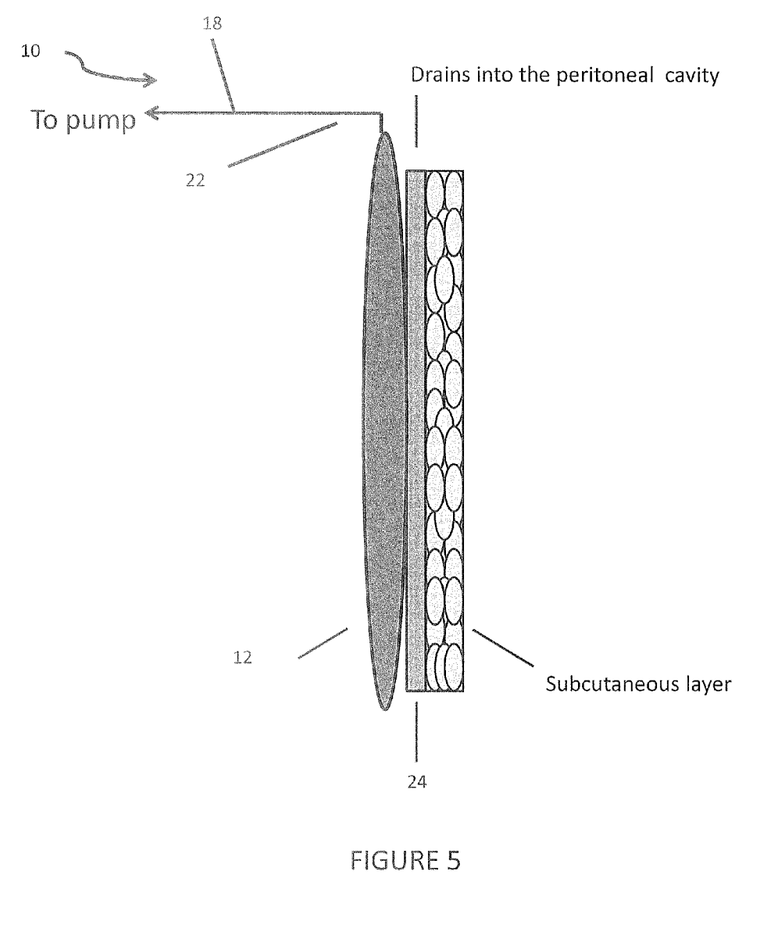
FIG. 5 is a cross-sectional view of a hydrophilic strip in contact with the volume-changing member and the subcutaneous tissue.
Figures 6, 7:
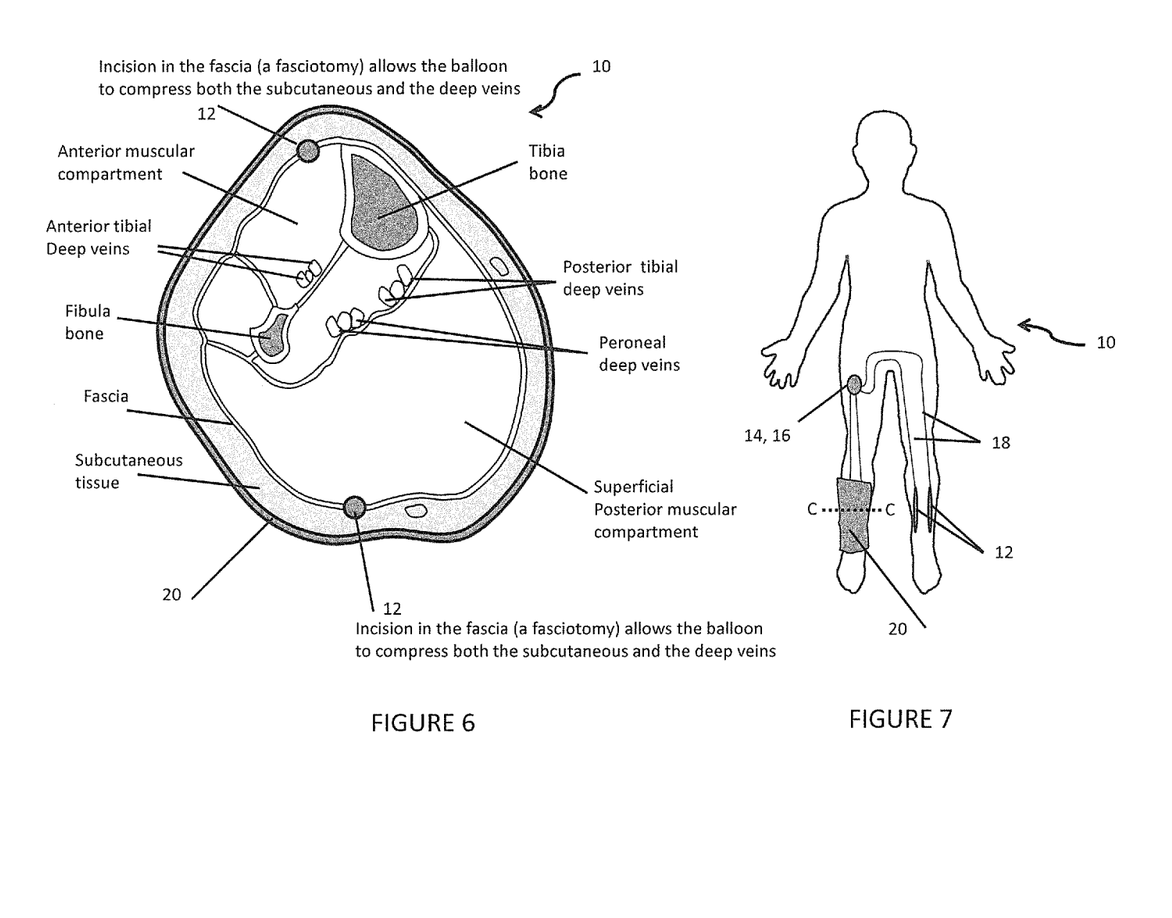
FIG. 6 is cross-sectional view along line C-C in FIG. 7 of the lower extremity showing volume-changing member placements within the anatomy, an incision in the fascia and a non-stretchable outer garment to target compression to the deep veins and subcutaneous tissue for symptoms related to venous insufficiency and lymphedema.
FIG. 7 is an illustration of the pulsatile pressure implant as applied to the lower extremity of an individual to target compression to the deep veins and subcutaneous tissue using a fasciotomy to treat symptoms related to venous insufficiency and lymphedema.

The pump 16 can be any suitable pump that can effectively cycle pressure. The target pressures are nominally 20 mmHg to 150 mmHg; however, other suitable pressures can also be used. For leg applications, the subcutaneous target pressure depends on the stage of skin rigidity but is of the order of approximately 100 mmHg at a rate of approximately 60 seconds for inflation and approximately 60 seconds for deflation with several seconds held at maximum pressure. The microprocessor-controlled electronics 14 and pump 16 can be worn external to the body as in FIG. 8, or it can be implanted as shown in FIGS. 2, 4, and 7.

The pumping efficiency can be improved by applying a strip with a hydrophilic coating 24 to the subcutaneous tissue. The hydrophilic strip 24 is used to absorb excess lymphatic fluid. As the volume-changing members 12 inflate against the saturated strip, the fluid is dispensed into the peritoneal cavity.

The tubing 18 carries biocompatible gas or liquid, such as, but not limited to, air or saline, between the pump 16 and the volume-changing members 12 in order to expand or contract the volume-changing members 12. The tubing 18 can be made of any biocompatible material, such as, but not limited to, organic polymers.

The pulsatile pressure implant 10 can also be used in combination with a lightweight non-stretchable, non-compressive outer garment, shown at 20 in FIGS. 3, 4, 6, and 7, made of a material such as nylon, silk, or equivalent, that is worn around the leg or arm on the outside of the body at the volume-changing member 12 location to create a counter-pressure to the outward volume-changing member pressure. The garment does not need to be compressive, it only needs to be non-stretchable, and therefore, light materials such as silk can be used. Preferably, the material slides easily onto the treatment area. The outer garment 20 can include a closure such as a zipper, hook and loop mechanism, or an elastic seam. A tighter outer garment 20 can be worn at the ankle to mitigate downward fluid flow and assist in directing fluid away from areas of pooling fluid. A medicated lining in the outer garment 20 can also be used to treat areas with open sores.

In order to use the pulsatile pressure implant 10, a surgeon can implant the various parts as needed. The volume-changing members 12 are implanted along with the microprocessor-controlled electronics 14, pump 16, and all necessary tubing 18. Alternatively, as described above, the microprocessor-controlled electronics 14 and pump 16 can remain external to the body but still connected to the volume-changing members 12 through the tubing within the body.

The volume-changing members 12 can be placed at various places within the anatomy of the lower legs or arms depending on the areas of targeted compression. The current state of the art treats patients with venous insufficiency the same as those with lymphedema, i.e. using untargeted external compression. By placing the volume-changing members 12 in strategic locations within the anatomy, the present invention targets the compression within the extremity and addresses specific disease states. Specifically, compression to the deep veins targets symptoms related to venous insufficiency and compression to the subcutaneous tissue targets symptoms related to lymphedema.

Figure 1:
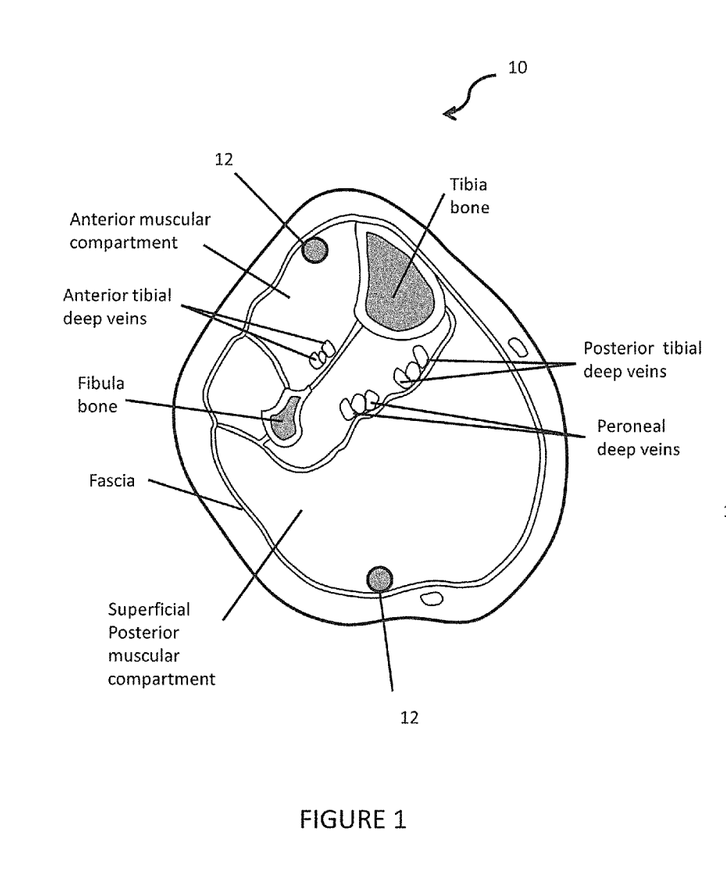
FIG. 1 is a cross-sectional view along line A-A in FIG. 2 of the lower extremity showing the placement within the anatomy of volume-changing members of the pulsatile pressure implant to target compression to the deep veins for symptoms related to venous insufficiency.

As shown in FIG. 1, by placing the volume-changing members 12 between the fascia and muscular compartment (i.e. subfascial compartment) compression is targeted to the deep veins. One volume-changing member 12 can be inserted between the fascia and the anterior muscular compartment. The second volume-changing member 12 can be inserted between the fascia and the superficial posterior muscular compartment, approximately 180 degrees from each other. The fascia acts as an inelastic band. When the volume-changing members 12 in each compartment expand, they push against the muscle. The muscle in turn compresses the deep veins, forcing the veins to narrow and improving blood circulation. The inelastic fascia contains the pressure within the inner compartments as the volume-changing members 12 expand and contract. In essence, there is an increase in pressure by the volume-changing members 12 in a minimally-expandable tube. The volume-changing members 12 augment the effects of muscle contractions around the deep veins of the individual, mimicking the ambulatory expansion and contraction of the calf muscles. In this case, the fascia takes the place of the outer garment 20 further described below.

Figure 3:
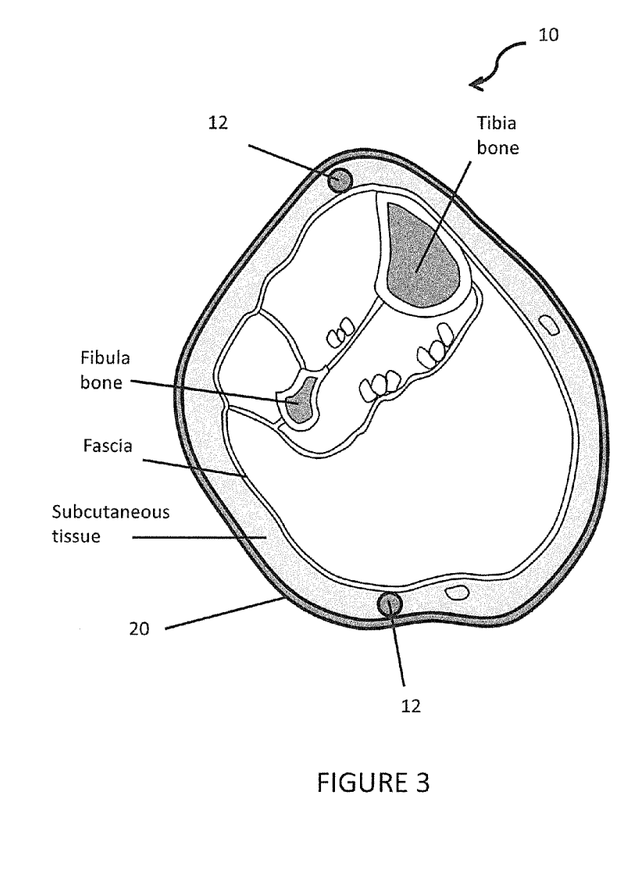
FIG. 3 is a cross-sectional view along line B-B in FIG. 4 of the lower extremity showing volume-changing member placements within the anatomy and a non-stretchable outer garment to target pulsatile compression to the subcutaneous tissue for symptoms related to lymphedema.

An alternative placement is shown in FIGS. 3 and 4. By placing the volume-changing members 12 between the fascia and subcutaneous tissue of the extremity, as the members expand the compression is targeted to the subcutaneous tissue where lymphatic fluid accumulates. The subcutaneous tissue, unlike the fascia, is not stiff so that when the volume-changing members 12 expand, the subcutaneous tissue also expands. To counteract this, the outer garment 20 can be worn around the leg or arm at the location where the volume-changing members 12 are implanted. The outer garment 20 prevents the subcutaneous tissue and the skin from expanding and enhances compression to the subcutaneous tissue as the volume-changing members 12 expand and contract and enhancing the movement of fluid out of the tissue.

In FIGS. 6 and 7, the volume-changing members 12 are used to compress both the subcutaneous tissue and the deep veins. The volume-changing members 12 are placed between the fascia and muscular compartment (i.e. subfascial compartment) similarly to FIG. 1, but in this case an incision is made in the fascia (i.e. a fasciotomy is performed). By making an incision in the fascia, this cuts through the tough, band-like fascia so that when the volume-changing members 12 expand, they compress both the subcutaneous tissue and the deep veins. The outer garment 20 can also be worn around the leg or arm at the location where the volume-changing members 12 are implanted. The outer garment 20 prevents the subcutaneous tissue and the skin from expanding and enhances compression to the subcutaneous tissue as the volume-changing members 12 expand and contract and improves the movement of fluid out of the tissue. Further, because the fascia has been compromised by the incision, the outer garment 20 contains the pressure from the volume-changing members 20 and enhances the compression to the deep veins.

In addition, the volume-changing members 12 can be placed in any other area between the fascia and muscular compartments of the leg to target the posterior tibial, anterior tibial, and peroneal deep veins.

The volume-changing members 12 can be placed within muscular compartments of the arm such as, but not limited to, the bicep and tricep brachial muscular compartments to target the brachial veins that branch into the radial and ulnar deep veins.

In general, the present invention provides for a method of treating venous insufficiency and lymphedema in an individual by placing pulsatile, localized compression on deep veins and subcutaneous tissue by expanding and contracting volume-changing members 12.

More specifically, once implanted in the extremity, the volume-changing members 12 are cyclically inflated and deflated using the biocompatible gas or liquid and the microprocessor-controlled electronics 14 including the pump 16 and an accelerometer (not shown). The accelerometer can be used to indicate whether the individual is standing or lying down so that the pressure amplitude can be adjusted in feedback accordingly. When expanded, the volume-changing members 12 constrict the deep veins or compress the subcutaneous tissue. When contracted, the volume-changing members 12 release the deep veins or subcutaneous tissue. The gas or liquid is transported through the tubing 18 that fluidly attaches the pump 16 to the volume-changing members 12. The implant 10 operates in feedback mode based on amplitude and cycle-frequency inputs, and inputs can also be manually adjusted with wireless communication to the implant 10. The inflation-deflation cycle of the volume-changing members 12 compresses the deep veins and improves blood circulation and/or compresses the subcutaneous tissue to improve lymphatic flow.

More specifically, the method can further include prior to the placing step, an insertion step such as inserting at least one volume-changing member between the fascia and a muscular compartment of the leg; inserting at least one volume-changing member between the fascia and muscular compartment of the arm; inserting at least one volume-changing member the fascia and subcutaneous tissue in the leg; inserting at least one volume-changing member between the fascia and subcutaneous tissue in the arm; performing a fasciotomy and inserting at least one volume-changing member between the fascia and a muscular compartment in the leg, and performing a fasciotomy and inserting at least one volume-changing member between the fascia and a muscular compartment in the arm; and combinations thereof.

An inelastic outer-garment worn around the location of the volume-changing members can be used in combination with the above to contain the pressure from the increase in volume from the volume-changing members and enhance the compression to the deep veins and subcutaneous tissue.

The at least one volume-changing member can be inserted in an extremity such as at least one arm, at least one leg, and combinations thereof. The microprocessor-controlled electronics, a pump, and tubing can be inserted in the individual remote from the at least one volume-changing member. As described above, the tubing can be optional if smart, volume-changing materials are used, and the microprocessor-controlled electronics can be controlled electronically.

The method can further include compressing and narrowing the diameter of the deep veins and causing an improvement in venous circulation, compressing the subcutaneous tissue and causing an increase in lymphatic flow, augmenting the effects of muscle movement around the deep veins and improving blood circulation and lymphatic flow and combinations thereof. Each of these actions can be accomplished according to the placement of the volume-changing members 12 as described above.

The compression by the volume-changing members 12 can be delivered in a pulsatile motion and with a gradient pressure depending on the type of volume-changing member 12 used, as described above. The method can further include the step of wearing the outer garment as described above.

Based on the different placements of the volume-changing members within the anatomy with or without the outer garment as described above, the present invention provides for different methods of potentiating venous and/or lymphatic circulation. The present invention provides for a method of potentiating venous circulation, by placing pulsatile, localized pressure that compresses the deep veins by expanding and contracting volume-changing members located between the fascia and muscular compartment, such that the increase in volume from the volume-changing members is transferred to deep veins, and augmenting the effects of muscle contractions around the deep veins and improving blood circulation.

The present invention provides for a method of potentiating lymphatic circulation, by placing pulsatile, localized pressure that compresses the subcutaneous tissue by expanding and contracting volume-changing members positioned between the fascia and subcutaneous tissue, such that the increase in volume from the volume-changing members is transferred to the subcutaneous tissue, optionally using a lightweight non-stretchable, non-compressive outer garment to contain the pressure from the increase in volume from the volume-changing members to the subcutaneous tissue, and supplementing muscle contractions and improving lymphatic flow.

The present invention further provides for a method of potentiating venous and lymphatic circulation, by creating an incision in the fascia, placing pulsatile, localized pressure that compresses the deep veins and subcutaneous tissue by expanding and contracting volume-changing members located between the fascia and muscular compartment, such that the increase in volume from the volume-changing members is transferred to deep veins and subcutaneous tissue, optionally using a lightweight non-stretchable, non-compressive outer garment to contain the pressure from the increase in volume from the volume-changing members to the deep veins and subcutaneous tissue, and augmenting the effects of muscle contractions around the deep veins and improving blood circulation and lymphatic flow.

The present invention has several advantages over the prior art. By making the device implantable, the user's daily activities are not obstructed and the device fits seamlessly into the patient's lifestyle, an important consideration for those with chronic conditions needing life-long treatment. By having all of the compression components implantable, the device addresses patients with skin breakdown and ulcerations that cannot tolerate external compression treatments. This method is not a major invasive surgery unlike what prior art implants require. The treatment is more effective than prior art methods since the compression can be targeted to the anatomy where the fluid burden resides. The implant allows for wireless communication so that the compression "prescription" (for example, the amplitude and cycle time) can be updated as needed by the prescribing physician. This, in effect, opens up a completely new way of treating individuals with venous insufficiency and lymphedema who need some form of continuous treatment to compensate for faulty venous valves or a compromised lymphatic system. Using a single, implantable device, the therapy can be altered as the symptoms of pain and swelling evolve from a treatment to maintenance phase. The present invention also mimics and enhances the natural mechanics of the anatomy. For example, in the lower extremity the motion of walking causes the calf muscles to contract, in turn squeezing the deep veins and improving blood circulation and the movement of subcutaneous fluid. Similarly, in the present invention, the inflatable membranes expand against the inner compartment muscles squeezing the deep veins, thereby increasing blood circulation and lymphatic flow. In addition, this augments the effects of natural muscle contractions within the anatomy.

The compounds used in the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of treating venous insufficiency and lymphedema in an individual, including the steps of:
    inserting at least one volume-changing member in a space between fascia and a muscular compartment or subcutaneous tissue, wherein the at least one volume-changing member does not wrap around a blood vessel or tissue and such that the at least one volume-changing member does not directly contact deep veins;
    placing pulsatile, localized pressure that compresses the deep veins or subcutaneous tissue by expanding and contracting the at least one solid volume-changing member with microprocessor-controlled electronics and a pump, such that the at least one volume-changing member pushes against muscle and the muscle compresses the deep veins; and further including the step of wearing a lightweight non-stretchable, non-compressive outer garment outside of the body at a location of the at least one volume-changing member, wherein the light weight non-stretchable, non-compressive outer garment creates a counter-pressure to the pulsatile, localized pressure from the increase in volume from the at least one volume-changing member to the deep veins and subcutaneous tissue.

2. The method of claim 1, wherein said inserting step is chosen from the group consisting of inserting at least one volume-changing member between the fascia and a muscular compartment of the leg; inserting at least one volume-changing member between the fascia and a muscular compartment of the arm; inserting at least one volume-changing member between the fascia and subcutaneous tissue of the leg; inserting at least one volume-changing member between the fascia and subcutaneous tissue of the arm; performing a fasciotomy and inserting at least one volume-changing member between the fascia and a muscular compartment in the leg and performing a fasciotomy and inserting at least one volume-changing member between the fascia and a muscular compartment in the arm; and combinations thereof.

3. The method of claim 2, wherein the at least one volume-changing member is inserted in an extremity chosen from the group consisting of at least one arm, at least one leg, and combinations thereof.

4. The method of claim 2, further including the step of inserting microprocessor-controlled electronics and a pump in the individual remote from the at least one volume-changing member.

5. The method of claim 2, further including the step of implanting the microprocessor-controlled electronics remote from the at least one volume-changing member and wirelessly controlling the at least one volume-changing member.

6. The method of claim 1, wherein said at least one volume-changing member is chosen from the group consisting of a balloon and a volume-changing material.

7. The method of claim 1, further including a step chosen from the group consisting of narrowing the diameter of the deep veins, compressing the subcutaneous tissue, augmenting the effects of muscle contractions around the deep veins and improving blood circulation and lymphatic flow, and combinations thereof.

8. The method of claim 1, further including the step of adjusting pressure amplitude and/or frequency according to feedback.

9. The method of claim 1, wherein said expanding step is further defined as the volume-changing member constricting the deep vein or subcutaneous tissue, and wherein said contracting step is further defined as the at least one volume-changing member releasing the deep vein or subcutaneous tissue.

10. The method of claim 1, further including the steps of applying a strip with a hydrophilic coating to subcutaneous tissue and absorbing excess lymphatic fluid.

11. A method of potentiating venous circulation, including the steps of:
    inserting at least one volume-changing member in a space between fascia and a muscular compartment or subcutaneous tissue, wherein the at least one volume-changing member does not wrap around a blood vessel or tissue and such that the at least one volume-changing member does not directly contact deep veins;

placing pulsatile, localized pressure that compresses the deep veins by expanding and contracting the at least one volume-changing member located between the fascia and muscular compartment with microprocessor-controlled electronics and a pump, such that the increase in volume from the volume-changing members is transferred to deep veins, and such that the at least one volume-changing member pushes against muscle and the muscle compresses the deep veins;

augmenting the effects of muscle contractions around the deep veins and improving blood circulation; and further including the step of wearing a lightweight non-stretchable, non-compressive outer garment outside of the body at a location of the at least one volume-changing member, wherein the light weight non-stretchable, non-compressive outer garment creates a counter-pressure to the pulsatile, localized pressure from the increase in volume from the at least one volume-changing member to the deep veins and subcutaneous tissue.

12. A method of potentiating lymphatic circulation, including the steps of:

inserting at least one volume-changing member in a space between fascia and subcutaneous tissue, wherein the at least one volume-changing member does not wrap around a blood vessel or tissue and such that the at least one solid volume-changing member does not directly contact deep veins;

placing pulsatile, localized pressure that compresses the subcutaneous tissue by expanding and contracting the at least one volume-changing member positioned between the fascia and subcutaneous tissue with microprocessor-controlled electronics and a pump, such that the increase in volume from the volume-changing members is transferred to the subcutaneous tissue such that the at least one volume-changing member pushes against muscle and the muscle compresses the deep veins;

supplementing muscle contractions and improving lymphatic flow; and further including the step of wearing a lightweight non-stretchable, non-compressive outer garment outside of the body at a location of the at least one volume-changing member, wherein the light weight non-stretchable, non-compressive outer garment creates a counter-pressure to the pulsatile, localized pressure from the increase in volume from the at least one volume-changing member to the deep veins and subcutaneous tissue.

13. A method of potentiating venous and lymphatic circulation, including the steps of:

creating an incision in the fascia;

inserting at least one volume-changing member in a space between fascia and a muscular compartment, wherein the at least one volume-changing member does not wrap around a blood vessel or tissue and such that the at least one volume-changing member does not directly contact deep veins;

placing pulsatile, localized pressure that compresses the deep veins and subcutaneous tissue by expanding and contracting the at least one volume-changing member located between the fascia and muscular compartment with microprocessor-controlled electronics and a pump, such that the increase in volume from the at least one solid volume-changing member is transferred to deep veins and subcutaneous tissue, and such that the at least one volume-changing member pushes against muscle and the muscle compresses the deep veins;

augmenting the effects of muscle contractions around the deep veins and improving blood circulation and lymphatic flow; and further including the step of wearing a lightweight non-stretchable, non-compressive outer garment outside of the body at a location of the at least one volume-changing member, wherein the light weight non-stretchable, non-compressive outer garment creates a counter-pressure to the pulsatile, localized pressure from the increase in volume from the at least one volume-changing member to the deep veins and subcutaneous tissue.

14. The method of claim 13, further including the step of using a lightweight non-stretchable, non-compressive outer garment to contain the pressure from the increase in volume from the volume-changing members to the deep veins and subcutaneous tissue.

15. A pulsatile pressure implant comprising:

at least one volume-changing member for placing pulsatile, localized pressure on deep veins and subcutaneous tissue between fascia and a muscular compartment, wherein the at least one volume-changing member does not wrap around a blood vessel or tissue and the at least one volume-changing member does not directly contact deep veins, wherein the at least one volume-changing member is in connection with microprocessor electronics, wherein said at least one volume-changing member is further in fluid connection with a pump for pumping fluid through tubing to expand said at least one volume-changing member, and wherein said microprocessor-controlled electronics provide feedback to said at least one volume-changing member based on whether an individual is standing or lying down; and further including a lightweight non-stretchable, non-compressive outer garment worn on an outside of the body at a location of the at least one volume-changing member, wherein the light weight non-stretchable, non-compressive outer garment creates a counter-pressure to the pulsatile, localized pressure from the increase in volume from the at least one volume-changing member to the deep veins and subcutaneous tissue.

16. The pulsatile pressure implant of claim 15, wherein said at least one volume-changing member is a balloon made of a material chosen from the group consisting of plastic, silicone, and elastomers.

17. The pulsatile pressure implant of claim 15, wherein said at least one volume-changing member includes a fill port.

18. The pulsatile pressure implant of claim 15, wherein said at least one volume-changing member is powered by a battery wirelessly charged.

19. The pulsatile pressure implant of claim 15, wherein said at least one volume-changing member is coated with a drug chosen from the group consisting of non-steroidal anti-inflammatory drugs (NSAIDS), steroids, and immune selective anti-inflammatory derivatives (ImSAIDs).

20. The pulsatile pressure implant of claim 15, wherein said at least one volume-changing member is coated with a hydrophilic material.

21. The pulsatile pressure implant of claim 15, wherein said at least one volume-changing member includes a single chamber and provides pulsatile pressure.

22. The pulsatile pressure implant of claim 15, wherein said microprocessor-controlled electronics is controlled wirelessly and remotely.

23. The pulsatile pressure implant of claim 15, wherein said tubing includes a biocompatible fluid chosen from the group consisting of air and saline that expands said expandable mechanisms.

* * * * *